United States Patent
Baek et al.

(10) Patent No.: US 6,552,195 B1
(45) Date of Patent: Apr. 22, 2003

(54) QUINOXALINE-CONTAINING AB$_2$ MONOMERS FOR HYPERBRANCHED AROMATIC POLYAMIDES

(75) Inventors: Jong-Beom Baek, Beavercreek, OH (US); Loon-Seng Tan, Centerville, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 10/083,963

(22) Filed: Feb. 27, 2002

(51) Int. Cl.$^7$ .............................. C07D 241/42
(52) U.S. Cl. ....................................... 544/353
(58) Field of Search ......................... 544/353

(56) References Cited

U.S. PATENT DOCUMENTS 4,125,725 A * 11/1978 Duffy .................... 544/353

OTHER PUBLICATIONS

Jong–Beom Baek, John B. Ferguson, Patrick T. Mather, Loon–Seng Tan, *Hyperbranched Aromatic Polyamides Containing Ether and Quinoxaline Units and Their Blends with BMI*, Polymeric Materials: Science & Engineering, 2001, 84, 724–5, Published about Mar. 15, 2001.

* cited by examiner

*Primary Examiner*—Emily Bernhardt
(74) *Attorney, Agent, or Firm*—Charles E. Bricker; Thomas L. Kundert

(57) ABSTRACT

AB$_2$ monomers of the formula

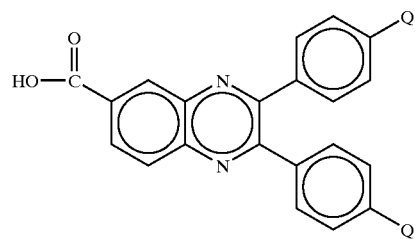

wherein Q is

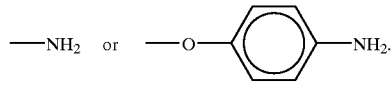

Polymerization of these monomers results in hyperbranched aromatic polyamides.

2 Claims, No Drawings

QUINOXALINE-CONTAINING AB$_2$ MONOMERS FOR HYPERBRANCHED AROMATIC POLYAMIDES

RIGHTS OF THE GOVERNMENT

The invention described herein may be manufactured and used by or for the Government of the United States for all governmental purposes without the payment of any royalty.

BACKGROUND OF THE INVENTION

The present invention relates to novel amine-terminated hyperbranched quinoxaline-amide polymers as room-temperature initiators for bismaleimide polymerization.

Historically, fabrication of high performance, organic matrix composite (OMC) structures for aircraft and space systems applications on a low volume basis is very costly. This is because nonrecurring costs such as tooling and capital equipment are the major cost drivers for low volume production. Thus, there is a pressing need to reduce the costs of OMC structures, for both prototype and low-volume programs. Since autoclaves and hardened tooling, traditionally required for the fabrication of large, composite-based spacecraft components, have the lion's share in the fabrication cost, the affordability issue can be logically addressed by developing non-autoclave resins and processing. Toward this end, there are currently two approaches, namely, low-temperature curing and electron-beam (E-beam) curing. In the former, the objective is to drastically lower the curing temperature and pressure for composites so that tooling can be fabricated easily from relatively inexpensive materials, such as wood, fiberglass, or foam. However, for these processing conditions, the material systems (prepreg, liquid resin and adhesive) must possess characteristics that are conducive to low temperature/low pressure processing (e.g., 150° F. and 14 psi), and, after post-cure in free-standing fashion, should provide structural performance equivalent to current aerospace standards (e.g. epoxy-3501). This approach is hampered by the lack of suitable material systems that can be cured at temperatures below 65° C. to form structures with high temperature properties. An alternative approach to low-temperature thermal cure is E-beam curing. Although this method of curing is rapid (seconds to minutes as opposed to hours for thermal curing), a high-energy, electron-beam source (<250 KeV to >1 MeV) is required, necessitating some measures of personnel protection.

Bismaleimide (BMI) resins are attractive for composite applications because such resins can be processed and fabricated similar to epoxies and their use temperatures are much higher. However, the curing temperatures of BMI are generally in excess of 200° C. Therefore, it is desirable to lower the polymerization temperatures to below 65° C. and at the same time preserve the high temperature properties from conventional thermal cure of BMI resins.

Dendritic macromolecules such as dendrimers and hyperbranched polymers are a new class of highly branched polymers that have distinctly different properties from their linear analogs Both dendrimers and hyperbranched polymers have much lower solution and melt viscosities than their linear analogs of similar molecular weights. They also have a large number of chain-ends whose collective influence dictates their overall physical and/or chemical behaviors. These features are attractive in terms of processability and offer flexibility in engineering-required properties for specific applications.

Hyperbranched polymers have an important and practical advantage over dendrimers at the "raw material" level. Although dendrimers have precisely controlled structures (designated as generations), their preparations generally involve tedious, multi-step sequences that are impractical and costly in scale-up production. Synthesis of a hyperbranched polymer, on the other hand, is a one-pot process. Large quantities of hyperbranched polymers can be easily produced from AB$_x$ (x $\geq$ 2) monomers.

Accordingly, it is an object of the present invention to provide novel quinoxaline-containing monomers AB$_2$ monomers for hyperbranched aromatic polyamides.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided AB$_2$ monomers for hyperbranched aromatic polyamides of the formula

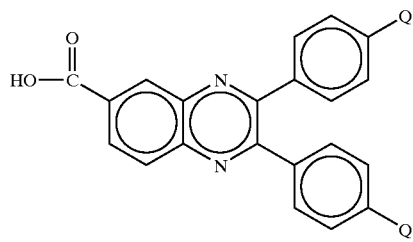

wherein Q is

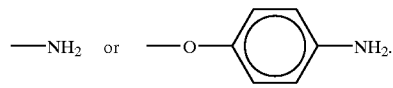

DETAILED DESCRIPTION OF THE INVENTION

The AB$_2$ monomers of this invention can be synthesized as described in the Examples which follow.

These monomers can be polymerized to provide polymers having the following repeating units:

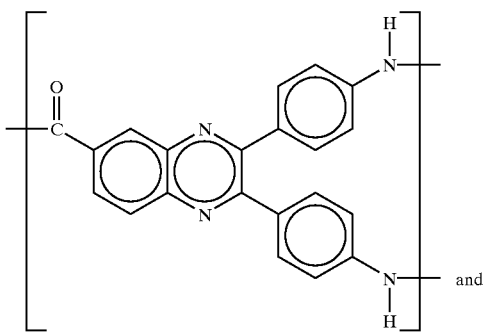

and

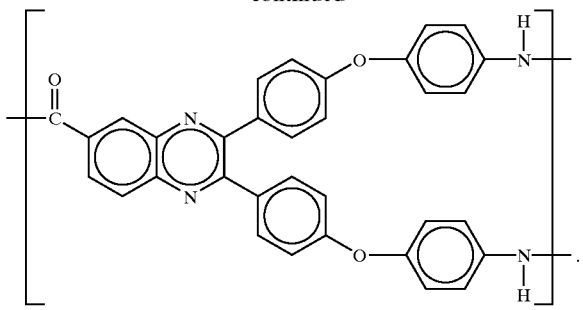

Aromatic polyamides are prepared via two general routes: (i) polycondensation reaction via an aromatic diacid chloride and a diamine and (ii) direct polycondensation reaction of a dicarboxylic acid and a diamine. For route (i), because of the extreme moisture sensitivity of diacid chlorides and the highly exothermic nature of the reaction between an amine and a carboxylic acid chloride, the polymerization is usually conducted at temperatures at or below 0° C. and under inert atmosphere. In addition, in order to consistently achieve high molecular weight for the resulting polyamides, the diacid chloride monomers must be freshly purified prior to polymerization. For route (ii), since the dicarboxylic acid monomers are cheaper, much less sensitive to moisture and relatively easy to purify via recrystallization, the polycondensation is more amenable to scale-up. However, because of little or no formation of amide from a carboxylic acid and an amine under ambient conditions, a phosphorus (V)-based promoter is used to activate the carboxylic group. The Yamazaki reaction embodies the most commonly used conditions that employ triphenyl phosphite (TPP) in N-methylpyrrolidinone (NMP) solution containing lithium chloride or calcium chlorides at 100° C.

The polymers can be employed to initiate bismaleimide polymerization. Another application of these polymers is to increase the toughness for thermosets such as BMI and epoxies. By the term toughness is meant resistance to impact induced damage. Toughness in cured neat resin samples may be assessed by the critical stress intensity factor, $K_{1C}$, among others. Toughness in fiber reinforced composites prepared by laying up and subsequently curing numerous plies of prepregs is best assessed by measuring the compression strength after an impact of suitable energy. Generally, an impact of 1500 in-lb/in is used, and compression after impact (CAI) values measured in accordance with Boeing test BSS 7260 on a quasiisotropic $[+45/0/-45/90]_{4s}$ layup. Alternatively, other measures of toughness such as laminate $G_{IIC}$ are used.

The following examples illustrate the invention:

EXAMPLE 1

2-Benzoyloxy-2-(4-nitrophenyl)acetonitrile (Cyano (4-nitrophenyl)methyl benzoate)

Into a 500 mL three-necked, round-bottomed flask equipped with a magnetic stirrer and nitrogen inlet, 4-nitrobenzaldehyde (50.0 g, 331 mmol) and benzoyl chloride (50 mL) were dissolved in dichloromethane (50 ml). Potassium cyanide (33.0 g, 507 mmol) in water (100 mL) was added dropwise at an ice-bath temperature. Triethylbenzylammonium chloride (TEBA, 2.5 g) was added and the resulting two-phase system was stirred for 24 h at room temperature. Organic layer was diluted with dichloromethane (100 mL), separated, washed with aqueous sodium bicarbonate, and dried over magnesium sulfate. After $CH_2Cl_2$ had been completely removed from the extract, the resulting light orange residue was dissolved in warm ethanol and cooled to room temperature to give 65.4 g (70% yield) of off-white crystals: mp 114–116° C. (lit. mp 116–117.5° C.). Anal. Calcd. for $C_{15}H_{10}N_2O_4$: C, 63.83%; H, 3.57%; N, 9.92%; O, 22.67%. Found: C, 63.96%; H, 3.62%; N, 9.42%; O, 23.71%. FT-IR (KBr, cm$^{-1}$): 1733, 2923. Mass spectrum (m/e): 282 (M$^+$, 100% relative abundance), 255, 225, 105.). $^1$H-NMR (CDCl$_3$, ppm) δ6.79 (s, 1H, CH), 7.47–7.53 (t, 2H, Ar), 7.63–7.66 (t, 1H, Ar), 7.82–7.75 (dd, 2H, Ar), 8.06–8.09 (dd, 2H, Ar), 8.33–8.36 (dd, 2H, Ar). $^{13}$C-NMR (CDCl$_3$, δ in ppm): 62.23, 115.25, 124.12, 127.46, 128.87, 130.16, 134.57, 138.28, 149.03, 164.32.

EXAMPLE 2

2-Benzoyloxy-1,2-bis(4-nitrophenyl)ethanone

Into a 1000 mL three-necked, round-bottomed flask equipped with a magnetic stirrer and nitrogen inlet, 2-benzoyloxy-2-(4-nitrophenyl)acetonitrile (42.0 g, 149 mmol) in benzene (450 mL), 10% sodium hydroxide (30 mL), and TEBA (2.2 mg) were stirred for 10 min under the nitrogen. Then, 4-nitrobenzaldehyde (22.52 g, 149 mmol) in benzene (100 mL) was added at ice-bath temperature and the resulting mixture was stirred for 4 h at room temperature. The organic layer was separated, washed with water, dried over magnesium sulfate. After the solvent had been removed via a rotovap, the resulting residue was dissolved in ethanol and cooled to room temperature to give 69.6 g (77% yield) of off-white crystals, mp 131–133° C. (lit. mp 132–134° C.). Anal. Calcd. for $C_{21}H_{14}N_2O_7$: C, 62.07%; H, 3.47%; N, 6.89%. Found: C, 62.26%; H, 3.36%; N, 6.77%. FT-IR (KBr, cm$^{-1}$): 1701, 1720. Mass spectrum (m/e): 406, 150 (M$^+$, 1% relative abundance).

EXAMPLE 3

4,4'-Dinitrobenzil (1,2-bis(4-dinitrophenyl)ethane-1, 2-dione)

Into a 500 mL three-necked, round-bottomed flask equipped with a magnetic stirrer, dropping funnel and nitrogen inlet, 2-benzoyloxy-1,2-bis(4-nitrophenyl)ethanone (15.0 g, 36.9 mmol) was dissolved in DMSO (dimethyl sulfoxide) (150 mL) and stirred until the solution become homogeneous. Then, hydrobromic acid (48%, 50 mL) was added through dropping funnel and stirred at 60° C. During this process, light yellow crystals were separated from the reaction mixture. After the reaction mixture had been allowed to cool down on its own, the crystals were collected by suction filtration, 10.1 g (91% yield), mp 211–212° C. Anal. Calcd. for $C_{21}H_{12}N_4O_6$: C, 56.01%; H, 2.69%; N, 9.33%; O, 31.97%. Found: C, 55.75%; H, 2.50%; N, 9.30%; O, 33.98%: FT-IR (KBr, cm$^{-1}$): 1347, 1527, 1682. Mass spectrum (m/e): 282 (M$^+$, 100% relative abundance). $^1$H-NMR (DMSO-d6, δ in ppm): 8.27–8.30 (dd, 4H, Ar), 8.41–8.44 (dd, 4H, Ar). $^{13}$C-NMR (DMSO-d$_6$, δ in ppm) 123.94, 131.66, 136.81, 150.75, 190.06.

EXAMPLE 4

2,3-Bis(4-nitrophenyl)-quinoxaline-6-carboxylic Acid

Into a 250 mL three-necked round-bottomed flask equipped with a magnetic stirrer, a condenser, and nitrogen inlet, 4,4'-dinitrobenzil (8.2 g, 27.3 mmol) and 3,4-diaminobenzoic acid (4.4 g, 28.9 mmol) were dissolved in acetic acid (100 mL) and heated under reflux for 12 h. After cooling to room temperature, the dark red solution was filtered and the filtrate was poured into 5% hydrochloric acid. The resulting precipitate was collected by suction filtration and air-dried to give 11.1 g (98% yield) of off-white powder, mp 287–289° C. Anal. Calcd. for $C_{21}H_{12}N_4O_6$: C, 60.58%; H, 2.91%; N, 13.46%; O, 23.06%. Found: C, 60.25%; H, 3.10%; N, 13.12%; O, 24.84%. FT-IR (KBr, cm$^{-1}$): 1521, 1670. Mass spectrum (m/e): 419 (M$^+$, 100% relative abundance). $^1$H-NMR (DMSO-d$_6$, ppm) δ7.78–7.81 (d, 4H, Ar), 8.24–8.27 (d, 4H, Ar), 8.30 (s, 1H, Ar), 8.36–8.37 (d, 1H, Ar), 8.39–8.40 (d, 1H, Ar), 8.68–8.69 (d, 1H, Ar). $^{13}$C-NMR (DMSO-d$_6$, δ in ppm): 123.34, 129.44, 130.31, 130.74, 131.29, 139.81, 142.31, 144.04, 147.61, 147.67, 152.16, 152.80, 166.27, 171.89.

EXAMPLE 5

2,3-Bis(4-aminophenyl)-quinoxaline-6-carboxylic Acid

Into a 500 mL high pressure bottle, 2,3-bis(4-nitrophenyl)-quinoxaline-6-carboxylic acid (8.0 g, 19 mmol), palladium on activated carbon (10%, 0.5 g), and mixture of ethanol (100 mL) and acetone (50 mL) were placed. The bottle was placed on a Parr hydrogenator. Hydrogen was charged and discharged five times and the reaction mixture was agitated at 60–65 psi for 24 h. After the final reaction mixture had been filtered through a cake of Celite 545 to remove catalyst, the solvent was removed from the filtrate on a rotovap. The gray solid was slurried in deoxygenated 2-propanol and collected by suction filtration to give 5.2 g (76.5% yield) of orange powder; mp 187–195° C. Anal. Calcd. for $C_{21}H_{16}N_4O_2$: C, 70.78%; H, 4.53%; N, 15.72%; O, 8.98%. Found: C, 69.26%; H, 5.78%; N, 13.86%; O, 10.50%. FT-IR (KBr, cm$^{-1}$): 1670, 3356. Mass spectrum (m/e): 358, 360 (M$^+$, 100% relative abundance). 1H-NMR (DMSO-d$_6$, ppm) δ6.29–6.33 (dd, 4H, Ar), 6.48–6.56 (m, 4H, Ar), 6.62–6.76 (m,1H, Ar), 7.10–7.18 (m, 2H, Ar). $^{13}$C-NMR (DMSO-d$_6$, δ in ppm): 57.19, 58.23, 110.87, 112.83, 112.97, 113.78, 115.10, 117.41, 118.67, 120.20, 128.20, 128.38, 128.72, 129.24, 132.70, 138.51, 146.72, 146.81, 157.17, 167.92

EXAMPLE 6

2,3-Bis(4-methoxyphenyl)-quinoxaline-6-carboxylic Acid

Into a 500 mL three-necked, round-bottomed flask equipped with a magnetic stirrer, nitrogen inlet, and a condenser, 3,4-diaminobenzoic acid (14.2 g, 93.4 mmol) was completely dissolved in acetic acid (300 mL). 4,4'-dimethoxybenzol (25.0 g, 92. mmol) was then added and the resulting reaction mixture was heated under reflux for 8 h. While the red-brown mixture was allowed to cool down on its own, light orange needles formed and separated from the mother liquid; 34.8 g (97% crude yield, mp 295–297° C. Anal. Calcd. for $C_{23}H_{18}N_2O_4$: C, 71.49%; H, 4.70%; N, 7.25%: Found: C, 71.51%; H, 4.45%; N, 6.96%. FT-IR (KBr, cm$^{-1}$): 1693. Mass spectrum (m/e): 386 (M$^+$, 100% relative abundance). 1H-NMR (DMSO-d$_6$, δ in ppm): 3.80 (s, 6H, CH3), 6.93–6.96 (d, 4H, Ar), 7.45–7.49 (dd, 4H, Ar), 8.12–8.15 (d, 1H, Ar), 8.22–8.26 (dd, 1H, Ar), 8.58–8.59 (d, 1H, Ar). $^{13}$C-NMR (DMSO-d$_6$, ppm) δ55.12, 113.55, 128.92, 130.48, 130.74, 131.08, 131.17, 131.52, 139.41, 142.11, 153.49, 154.09, 159.88, 159.97, 166.59.

EXAMPLE 7

2,3-Bis(4-hydroxyphenyl)-quinoxaline-6-carboxylic Acid

Into a 1000 mL three-necked round-bottomed flask equipped with a magnetic stirrer, nitrogen inlet, and a condenser, 2,3-bis(4-methoxyphenyl)-quinoxaline-6-carboxylic acid (34.7 g, 89.8 mmol) was dissolved in acetic acid (260 mL). Hydrobromic acid (500 mL) was then added to the clear, yellow mixture at room temperature. The reaction mixture was heated under reflux with vigorous stirring until the solution become homogeneous. After the red-brown mixture had been allowed to cool down on its own, it was poured into distilled water. The resulting light brown precipitate was collected by suction filtration and dried under the reduced pressure to give 31.9 g (99% crude yield) of yellow solid: mp 319–320° C. (dec.). Anal. Calcd. for $C_{21}H_{14}N_2O_4$: C, 70.38%; H, 3.94%; N, 7.82%. Found: C, 66.70%; H, 3.98%; N, 7.20%. FT-IR (KBr, cm$^{-1}$): 1698, 3396. Mass spectrum (m/e): 358 (M$^+$, 100% relative abundance). $^1$H-NMR (DMSO-d$_6$, ppm) δ6.76–6.79 (d, 4H, Ar), 7.36–7.40 (dd, 4H, Ar), 8.09–8.12 (d, 1H, Ar), 8.21–8.25 (dd, 1H, Ar), 8.57 (d, 1H, Ar). $^{13}$C-NMR (DMSO-d$_6$, δ in ppm): 114.93, 128.84, 129.21, 130.34, 131.11, 131.52, 139.32, 142.03, 153.75, 154.35, 158.44, 166.68.

EXAMPLE 8

2,3-Bis(4-nitrophenyloxyphenyl)-quinoxaline-6-carboxylic Acid

Into a 250 mL three-necked, round-bottomed flask equipped with a magnetic stirrer, nitrogen inlet, and a condenser, 4-fluoronitrobenzene (8.3 g, 57 mmol), 2,3-bis(4 hydroxyphenyl)-quinoxaline-6-carboxylic acid (10.0 g, 28 mmol), potassium carbonate (14.0 g, 100 mmol), and a mixture of NMP (110 mL) and toluene (60 mL) were placed. The reaction mixture was then heated and maintained around 140° C. for 8 h with vigorous nitrogen flow. The dark solution was filtered while it was still warm and the filtrate was poured into distilled water containing 5% hydrochloric acid. The resulting precipitates were collected by suction filtration and air-dried. Bright yellow crude product was boiled in acetic acid and filtered while hot to afford 16.4 g (98% yield) of light yellow powder, mp 252–254° C. Anal. Calcd. for $C_{33}H_{20}N_4O_8$: C, 66.00%; H, 3.36%; N, 9.33%; O, 21.31%. Found: C, 65.72%; H, 3.55%; N, 9.24%; O, 21.37%. FT-IR (KBr, cm$^{-1}$): 1586, 1701. Mass spectrum (m/e): 600 (M$^+$, 100% relative abundance). $^1$H-NMR (DMSO-d$_6$, δ in ppm): 7.13–7.18 (d, 4H, Ar), 7.26–7.29 (d, 4H, Ar), 7.62–7.65 (d, 4H, Ar), 8.21–8.24 (dd, 4H, Ar), 8.28 (s, 1H, Ar), 8.32–8.36 (dd, 1H, Ar), 8.68–8.69 (d, 1H, Ar). $^{13}$C-NMR (DMSO-d$_6$, δ in ppm): 117.58, 120.11, 126.13, 129.21, 132.12, 132.24, 135.29, 142.34, 153.40, 154.04, 154.96, 155.04, 162.39, 166.45.

EXAMPLE 9

2,3-Bis(4-aminophenyloxyphenyl)-quinoxaline-6-carboxylic Acid

Into a 500 mL high pressure bottle, 2,3-bis(4-nitrophenoxyphenyl)-6-carboxyquinoxaline (13.3 g, 22.1 mmol), palladium on activated carbon (10%, 0.5 g), and mixture of ethanol (150 mL) and acetone (150 mL) were placed. The bottle was placed on a Parr hydrogenator. Hydrogen gas was charged and discharged five times and the reaction mixture was then agitated mechanically at 60–65 psi for 24 h. After the resulting mixture had been filtered through a cake of Celite 545 to remove catalyst, the solvent was removed on rotovap. The yellow solid was poured into deoxygenated water. The resulting precipitate was collected to give 10.65 g (83.7% yield) of light yellow solids: mp 184.5° C. (dec.). Anal. Calcd. for $C_{33}H_{24}N_4O_4$: C, 73.32%; H, 4.47%; N, 10.36%; O, 11.84%. Found: C, 72.98%; H, 4.60%; N, 9.52%; O, 12.05%. FT-IR (KBr, cm$^{-1}$): 1705, 3373. Mass spectrum (m/e): 540 (M$^+$, 100% relative abundance). $^1$H-NMR (DMSO-d$_6$, δ in ppm): 6.77–6.80 (d, 4H, Ar), 6.88–6.91 (d, 8H, Ar), 7.48–7.51 (d, 4H, Ar), 8.25–8.28 (d, 1H, Ar), 8.29 (s, 1H, Ar), 8.60 (s,1H, Ar). $^{13}$C-NMR (DMSO-d$_6$, δ in ppm): 48.38, 116.11, 116.22, 116.60, 116.71, 116.86, 116.94, 118.85, 120.80, 120.89, 121.03, 129.24, 131.43, 131.75, 131.92, 142.14, 166.50.

Having thus described exemplary embodiments of the present invention, it should be noted by those skilled in the art that the disclosures herein are exemplary only and that alternatives, adaptations and modifications may be made within the scope of the present invention.

We claim:
1. 2,3-Bis(4-aminophenyl)-quinoxaline-6-carboxylic acid.
2. 2,3-Bis(4-aminophenyloxyphenyl)-quinoxaline-6-carboxylic acid.

* * * * *